(12) United States Patent
McCombe et al.

(10) Patent No.: US 7,549,993 B2
(45) Date of Patent: Jun. 23, 2009

(54) CONSTANT LIFT CAM SPREADER

(75) Inventors: Peter McCombe, Brisbane (AU); Eric Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 631 days.

(21) Appl. No.: 10/869,679

(22) Filed: Jun. 16, 2004

(65) Prior Publication Data

US 2005/0283161 A1    Dec. 22, 2005

(51) Int. Cl.
   *A61B 17/58*    (2006.01)
   *A61B 17/60*    (2006.01)
   *A61F 2/00*     (2006.01)

(52) U.S. Cl. ..................... 606/90; 606/86 R; 606/105; 606/246

(58) Field of Classification Search .............. 606/86, 606/90, 99, 105, 246–248, 279, 86 R; 81/349, 81/361, 383.5, 57.18, 443, 446, 453, 455, 81/90.2, 113, 143, 141, 138, 128, 485
See application file for complete search history.

(56) References Cited

U.S. PATENT DOCUMENTS

| | | | |
|---|---|---|---|
| 4,140,096 A * | 2/1979 | Dunn et al. ............... | 123/193.6 |
| 4,603,694 A | 8/1986 | Wheeler | |
| 4,736,738 A | 4/1988 | Lipovsek et al. | |
| 4,932,957 A | 6/1990 | Zwick | |
| 5,135,528 A | 8/1992 | Winston | |
| 5,191,917 A * | 3/1993 | Krumm et al. ............ | 139/380 |
| 5,201,519 A * | 4/1993 | Sorteberg ................. | 473/410 |
| 5,250,061 A | 10/1993 | Michelson | |
| 5,484,437 A | 1/1996 | Michelson | |
| 5,540,708 A | 7/1996 | Lim et al. | |
| 5,584,837 A | 12/1996 | Petersen | |
| 5,586,989 A | 12/1996 | Bray | |
| 5,620,447 A | 4/1997 | Smith et al. | |
| 5,658,336 A | 8/1997 | Pisharodi | |
| 5,782,830 A | 7/1998 | Farris | |
| 5,797,909 A | 8/1998 | Michelson | |
| 5,800,550 A * | 9/1998 | Sertich ..................... | 623/17.16 |
| 5,836,958 A | 11/1998 | Ralph | |
| 5,843,106 A | 12/1998 | Heisler | |
| 5,885,299 A | 3/1999 | Winslow et al. | |
| 5,888,224 A * | 3/1999 | Beckers et al. ........... | 623/17.16 |
| 5,893,890 A | 4/1999 | Pisharodi | |
| 6,001,113 A | 12/1999 | Goldblum | |
| 6,001,116 A | 12/1999 | Heisler et al. | |

(Continued)

OTHER PUBLICATIONS

Patent Cooperation Treaty—European Patent Office, "Notification of Transmittal of the Internatioinal Search Report and the Written Opinion of the International Searching Authority, or the Declaration," International Application No. PCT/US2005/021352, Nov. 15, 2005, 15 pages.

*Primary Examiner*—Eduardo C Robert
*Assistant Examiner*—Andrew Yang
(74) *Attorney, Agent, or Firm*—Haynes and Boone LLP (57) ABSTRACT

A cam spreader having a substantially rigid body with a proximal end defining a handle and a distal end defining a cam. The cam has at least a first lobe, the first lobe having an outer surface in a first quadrant of the cam as viewed in cross section along a longitudinal central axis of the body. At least a portion of the outer surface, or profile, of the curve is mathematically driven and produces a constant incremental lift.

16 Claims, 3 Drawing Sheets

U.S. PATENT DOCUMENTS

| | | |
|---|---|---|
| 6,004,326 A | 12/1999 | Castro et al. |
| 6,033,405 A | 3/2000 | Winslow et al. |
| 6,042,582 A | 3/2000 | Ray |
| 6,053,928 A | 4/2000 | Wyk et al. |
| 6,063,088 A | 5/2000 | Winslow |
| 6,080,158 A | 6/2000 | Lin |
| 6,083,225 A | 7/2000 | Winslow et al. |
| 6,093,207 A | 7/2000 | Pisharodi |
| 6,096,038 A | 8/2000 | Michelson |
| 6,174,311 B1 | 1/2001 | Branch et al. |
| 6,217,598 B1 | 4/2001 | Berman et al. |
| 6,228,022 B1 | 5/2001 | Friesem et al. |
| 6,245,072 B1 | 6/2001 | Zdeblick et al. |
| 6,267,763 B1 | 7/2001 | Castro |
| 6,290,724 B1 * | 9/2001 | Marino .................. 623/17.11 |
| 6,309,421 B1 | 10/2001 | Pisharodi |
| 6,368,325 B1 * | 4/2002 | McKinley et al. ............ 606/99 |
| 6,383,188 B2 | 5/2002 | Kuslich et al. |
| 6,398,793 B1 | 6/2002 | McGuire |
| 6,419,684 B1 | 7/2002 | Heisler et al. |
| 6,436,101 B1 | 8/2002 | Hamada |
| 6,443,956 B1 | 9/2002 | Ray |
| 6,468,279 B1 | 10/2002 | Reo |
| 6,478,800 B1 | 11/2002 | Fraser et al. |
| 6,500,206 B1 | 12/2002 | Bryan |
| 6,514,260 B1 | 2/2003 | Zdeblick et al. |
| 6,540,753 B2 | 4/2003 | Cohen |
| 6,569,168 B2 | 5/2003 | Lin |
| 6,595,995 B2 | 7/2003 | Zdeblick et al. |
| 6,599,291 B1 | 7/2003 | Foley et al. |
| 6,610,065 B1 | 8/2003 | Branch et al. |
| 6,635,060 B2 | 10/2003 | Hanson et al. |
| 6,648,895 B2 | 11/2003 | Burkus et al. |
| 6,666,866 B2 | 12/2003 | Martz et al. |
| 6,676,665 B2 | 1/2004 | Foley et al. |
| 6,679,886 B2 | 1/2004 | Weikel et al. |
| 6,679,897 B2 | 1/2004 | Josephson |
| 6,682,534 B2 | 1/2004 | Patel et al. |
| 6,696,073 B2 * | 2/2004 | Boyce et al. ................ 424/422 |
| 6,709,438 B2 | 3/2004 | Dixon et al. |
| 2003/0212394 A1 * | 11/2003 | Pearson et al. ................ 606/41 |
| 2004/0078079 A1 | 4/2004 | Foley |

* cited by examiner

CONSTANT LIFT CAM SPREADER

BACKGROUND

During medical procedures, including surgeries of various kinds, the need may arise to spread, or distract, bones or other anatomical parts away from one another. This may be done to allow access to an inner portion or cavity of the body, or to create proper clearance for insertion of additional instrumentation, or to create a better vantage point to observe tissues, organs, or systems. Often, the parts that are being spread or distracted are joined together by tightly bound tissue such as ligaments. This can lead to additional damage being done to the surrounding organs or tissues due to the distraction process. Additionally, further damage may be done because the surgeon may be unable to ascertain the additional stress that will be placed on the distracted body parts due to an additional degree of stress placed on the distractor being used.

One example of a surgical procedure in which distraction may be needed but where it may be difficult for the surgeon to gauge the incremental stress being placed upon adjacent distracted bones due to the additional load being placed on the distractor is intervertebral surgery. When discs within the spinal column are repaired or replaced, or during fusion techniques, the vertebrae adjacent to the damaged disc may need to be distracted to allow clearance to insert an implant or fusion device. The end plates of the vertebrae can be susceptible to breakage if too great a force is applied. Therefore what is needed is a device and method to address the above identified issues and similar issues involving the distraction of delicate tissues.

SUMMARY

The present disclosure introduces a cam spreader having a substantially rigid body with a proximal end defining a handle and a distal end defining a cam. The cam has a first lobe with an outer surface in a first quadrant of the cam as viewed in cross section along a longitudinal central axis of the body of the spreader. The first quadrant is defined by first and second orthogonal axes, with the first and second axes being orthogonal both to each other and to the central axis. The outer surface of the first lobe is defined by a first line segment intersecting the first axis at a first distance from the second axis, a second line segment intersecting the second axis at a second distance from the first axis. A segment of a curve connecting the two line segments is defined by a mathematical equation providing for a constant incremental lift.

The foregoing has outlined features of several embodiments so that those skilled in the art may better understand the detailed description that follows. Additional features will be described below that further form the subject of the claims herein. Those skilled in the art should appreciate that they can readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure.

BRIEF DESCRIPTION OF THE DRAWINGS

Aspects of the present disclosure are best understood from the following detailed description when read with the accompanying figures. It is emphasized that, in accordance with the standard practice in the industry, various features may not be drawn to scale. In fact, the dimensions of the various features may be arbitrarily increased or reduced for clarity of discussion.

DETAILED DESCRIPTION

The present invention relates generally to the field of orthopedic surgery and more particularly to instrumentation for vertebral procedures. It is to be understood that the following disclosure provides many different embodiments, or examples, for implementing different features of various embodiments. Specific examples of components and arrangements are described below to simplify the present disclosure. These are merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 1:
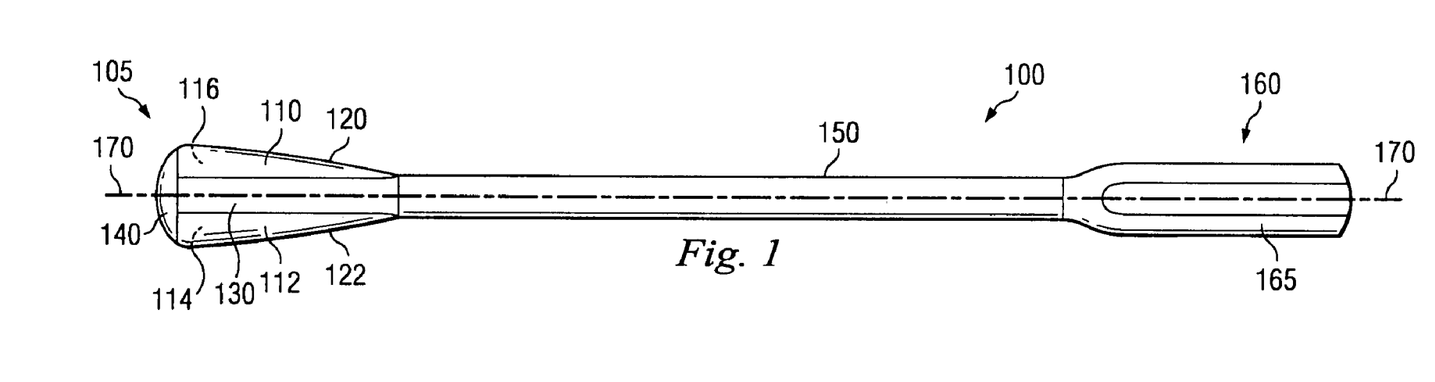
FIG. 1 is a top view of a constant lift cam spreader.
Figure 2:
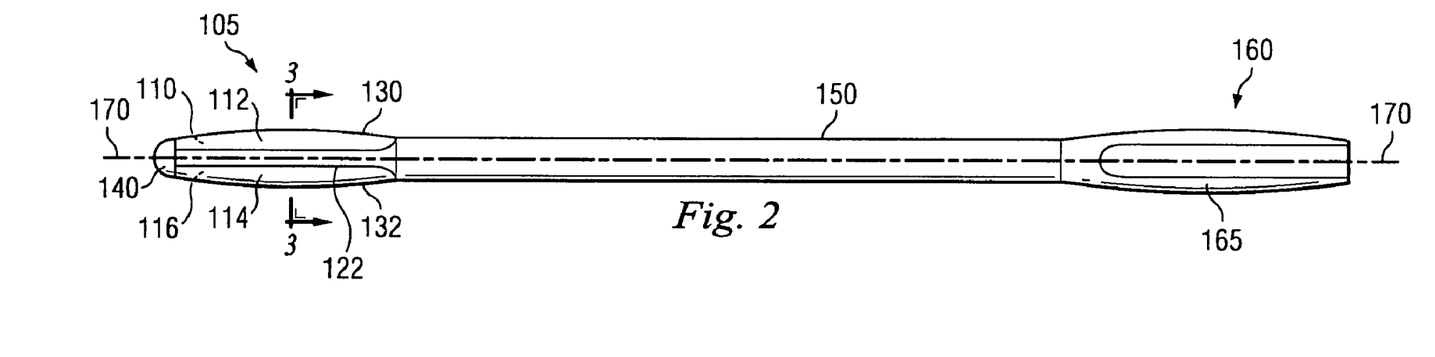
FIG. 2 is a side view of a constant lift cam spreader.

Referring to FIGS. 1-2 a top view and side view, respectively, of a constant lift cam spreader 100 is shown. A distal end 105 defining a series of cam lobes 110, 112, 114, 116, flat surfaces 120, 122, 130, 132 and a blunt tip 140 is shown. The distal end 105 joins to an elongated body 150 which may attach to a proximal end 160 defining a handle 165. The distal end 105, elongated body 150, and proximal end 160 may each be concentric to a single longitudinal axis 170.

The distal end 105 may be integral to the body 150 or they may be a separate components coupled together. The distal end 105 may be formed from steel, iron, aluminum, or other suitable metals or alloys. The distal end 105 may also be formed from plastics, polymers, ceramics, or other materials. In one embodiment, the distal end 105 is made from surgical grade stainless steel. The depth, length, and width of the distal end 105 may vary according to the application of the spreader 100. For example, a greater maximum available spread may require a greater width in the distal end 105.

The surfaces of the distal end 105, which define the cam lobes 110, 112, 114, 116, flat surfaces 120, 122, 130, 132 and tip 140 may be created by machining, casting, forging, or some other method depending upon the application of the spreader 100 and the material composition of the distal end 105. The surfaces 120-140 may have a brushed finish, a polished finish, or some other finish. In some embodiments, a separate coating (not shown) may be utilized to provide a desired surface texture. The distal end 105 may also comprise more or fewer surfaces than shown here and may also comprise multiple pieces that are coupled together to create the desired shape.

Shoulders or cam lobes 110, 112, 114, 116 may serve to provide an incremental lifting surface. Cam lobes 110, 112 join minimum lift flat surface 130 with maximum lift surfaces 120, 122 respectively. On the reverse side of the spreader 100, cam lobes 114, 116 join minimum lift surface 132 with maximum lift surfaces 120, 122, respectively. Thus a transition or incremental lift is provided between the minimum lift and the maximum lift provided by the spreader 100. The shape of the lobes 110, 112, 114, 116 may be defined by a mathematically driven curve, as explained in greater detail below.

The flat surfaces 120, 122, 130, 132 may be substantially flat or slightly curved and may serve to provide a stable location at which maximum or minimum lift is achieved by the spreader 100. The distance or spread between surfaces 130, 132 (the depth of the spreader 100) may be seen to be relatively smaller than the distance or spread between surfaces 120, 122 (the width of the spreader 100). By selecting the distance between surfaces 120 and 122, the maximum spread or lift of the spreader 100 may be chosen according to the purpose of the spreader 100. Similarly, by selecting the distance between the surfaces 130, 132, the minimum spread or lift of the spreader 100 may also be chosen according to the purpose of the spreader. The change in lift between minimum and maximum, or vice versa, occurs on the cam lobes 110, 112, 114, 116. A degree of lift that varies continuously between minimum and maximum lift may be provided on the cam lobes 110, 112, 114, 116. Additionally, as explained in greater detail below, the varying lift of the cam lobes 110, 112, 114, 116 may be configured to provide a constant degree of incremental lift with the change in lift being based directly on the amount of rotation imparted to the tool about the longitudinal axis 170.

The tip 140 of the spreader 150 may be sloped or tapered if needed. This may allow for easier insertion of the spreader 100 into an existing surgical opening or perforation. In some embodiments, the tip 140 may also be sharpened to a point. This may allow the spreader 100 to be used as a single tool that can both create an initial opening and then distract or enlarge the space or opening created. As with the other surfaces of the distal end 105, the tip 140 may be a separate component coupled to the distal end 105 or may be integral with the distal end 105.

The distal end 105 may also be integral to the body 150 of the spreader 100. In other embodiments, the distal end 105 may be detachable from the body 150. The body 150 may be formed from steel, iron, aluminum, or other suitable metals or alloys. The body 150 may also be formed from plastics, polymers, ceramics, or other materials according to need. In one embodiment, the body 150 is made from surgical grade stainless steel. The body 150 may be formed from casting, machining, or forging. The body 150 may have a surface finish corresponding to the application of the spreader 100. For example a highly polished and nonporous finish may be utilized where the spreader 100 is designed for use in a sterile surgical environment.

The dimensions of the body 150 may also be chosen according to the application of the spreader 100. For example, where the spreader 100 is needed for distraction deep within a surgical cavity, a longer body may be required than for distraction near the surface of a surgical incision. In cross section, the body 150 may be circular, but other shapes are also possible.

The body 150 may be integral with the proximal end 160, or the body 150 and proximal end 160 may be formed as separate components and coupled together. The proximal end 160 may define a handle 165. In FIGS. 1 and 2, the proximal end 160 is shown as defining a flat handle 165 corresponding to the general shape of the distal end 105. Other embodiments may have handles of other shapes however. For example, a tee shaped handle may be utilized to provide additional leverage. Additionally, a textured surface or grip (not shown) may be provided in addition to, or instead of, the handle 165 depending upon the application of the spreader 100.

Figure 3:
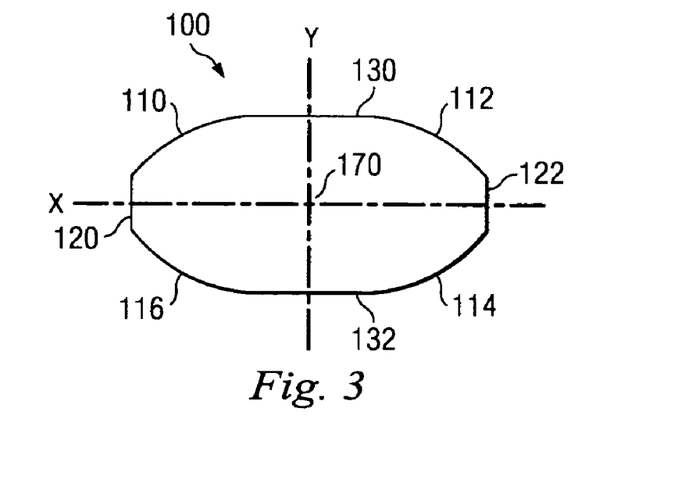
FIG. 3 is a cross sectional view of a constant lift cam spreader.

FIG. 3 is cross sectional view of a constant lift cam spreader 100. The view of FIG. 3 is taken along the line 3-3 as shown in FIG. 2. The axis 170 is orthogonal to the plane of FIG. 3 in the location shown. Axes X and Y serve to provide reference to the location of the central axis 170. Minimum spread surfaces 130, 132 are seen to be a smaller distance apart than maximum spread surfaces 120, 122. It can also be seen in this embodiment that the surfaces 130, 132 may be equidistant from the central axis 170. Similarly, surfaces 120, 122 may be equidistant from the central axis 170. Thus, lift or spread may also be defined in terms of the distance of the flat surfaces 120, 122, 130, 132 from the central axis 170. The shoulders, or cam lobes, 110, 112, 114, 116, are seen to provide a transition from minimum to maximum lift or vice versa about the central axis 170. The cam spreader may also be symmetric about the X axis and the Y axis.

Figure 4:
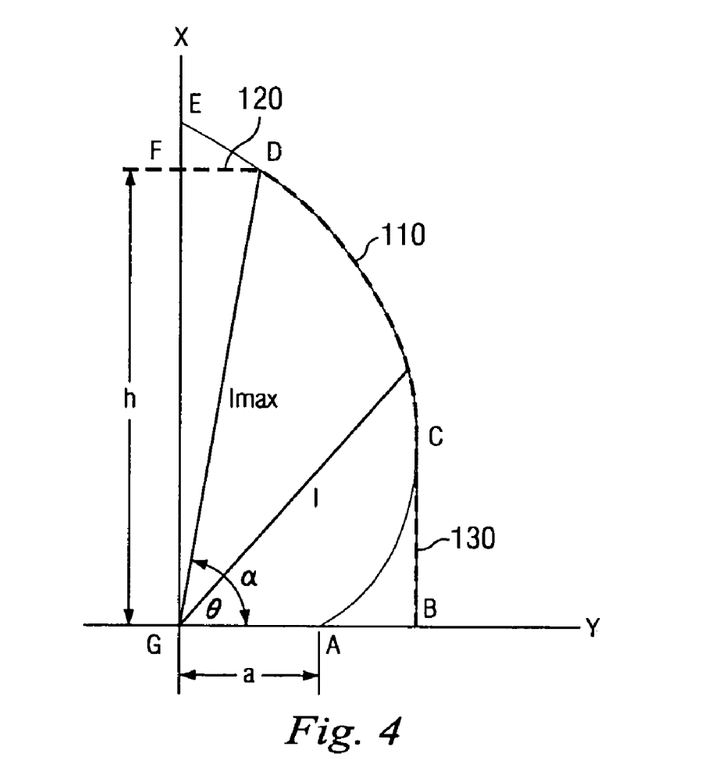
FIG. 4 is a plot from which one possible cam spreader shape may be derived.

FIG. 4 is a plot from which one possible cam spreader shape may be derived. With continued reference to FIG. 3, the plot of FIG. 4 may be seen to correspond to the upper left quadrant of FIG. 3, rotated 90° to simplify explanation. The plot or diagram of FIG. 4 illustrates a curve where the value of l increases in direct proportion to the angle θ. This describes the curve ACDE. Line BC is the vertical tangent to this curve and would form the side wall of a cam spreader tool or minimum lift surface 130. DF represents the flat surface on the top of the spreader, or a portion of the maximum lift surface 120. Here the maximum lift provided by the spreader 100 relative to the central axis 170 is represented by h, which is a constant. The symbol α represents the constant angle from the y axis 170 to the beginning of maximum lift surface 120. Thus GBCDF represents one quadrant of the cross section of the spreader 100. Here, the area bounded by GBCDF corresponds to the upper left quadrant of FIG. 3. Additionally, as explained in greater detail below, α is the y intercept of curve ACDE and is a variable parameter.

From FIG. 4 it may be seen that $$\sin \alpha = h/l_{max}$$

$$\therefore l_{max} = h/\sin \alpha \quad (1)$$

In the case of a cam with constant lift, the lift may be expressed in terms of a change in lift relative to a degree to rotation of the spreader 100, therefore $$\frac{dl}{d\theta} = k \quad (2)$$

where k is a constant lift which may be measured in mm/rad.

$$k = \frac{\text{lift}}{\text{angle}} \quad (3)$$

$$k = \frac{l_{max} - a}{\alpha}$$

$$k = \frac{\left(\frac{h}{\sin\alpha} - a\right)}{\alpha}$$

Returning to equation (2):

$$\frac{dl}{d\theta} = k$$

Integrating with respect to θ yields:

$$\therefore l = k\theta + C \tag{4}$$

where C is constant of integration. To determine the constant of integration, the condition where $\theta=\alpha$, $l=l_{max}$ as seen in FIG. 4 may be used, thus:

$$\frac{h}{\sin\alpha} = k\alpha + C \tag{3}$$

$$\therefore C = \frac{h}{\sin\alpha} - k\alpha$$

Returning to equation (4) and replacing C with its equivalent from equation (3) yields:

$$l = k\theta + \frac{h}{\sin\alpha} - k\alpha \tag{5}$$

Similarly, substituting the value for k from equation (2) into equation (5) yields:

$$l = \frac{\left(\frac{h}{\sin\alpha} - a\right)}{\alpha}\theta + \frac{h}{\sin\alpha} - \frac{\left(\frac{h}{\sin\alpha} - a\right)}{\alpha}\alpha, \tag{6}$$

which may be simplified to:

$$l = \frac{\left(\frac{h}{\sin\alpha} - a\right)}{\alpha}\theta + a$$

Thus, as shown above, a single equation in polar form may be used to represent the curve ACDE of FIG. 4. However, as will be shown below, it may be useful to work with a parametric representation of the curve ACDE. Therefore:

$$x = l\cos\alpha$$

$$y = l\sin\alpha$$

$$\therefore x = \left[\frac{\left(\frac{h}{\sin\alpha} - a\right)}{\alpha}\theta + a\right]\cos\theta \tag{7}$$

$$\therefore y = \left[\frac{\left(\frac{h}{\sin\alpha} - a\right)}{\alpha}\theta + a\right]\sin\theta \tag{8}$$

In both the radial form (equation (6)) and the parametric form (equations (7) and (8)) of the equation a value for the parameter a may be determined which will result in the curve ACDE being parallel to the Y axis at a distance from the Y axis corresponding to the chosen minimum lift provided by the spreader 100. To determine the values of parameter α that will satisfy this condition, it is necessary to take the first derivative of the equations in parametric form (equations (7) and (8)) with respect to θ. Thus:

$$\frac{dx}{d\theta} = \frac{\left(\frac{h}{\sin\alpha} - a\right)}{\alpha}\cos\theta - \left[\frac{\left(\frac{h}{\sin\alpha} - a\right)}{\alpha}\theta + a\right]\sin\theta \tag{9}$$

$$\frac{dy}{d\theta} = \frac{\left(\frac{h}{\sin\alpha} - a\right)}{\alpha}\sin\theta + \left[\frac{\left(\frac{h}{\sin\alpha} - a\right)}{\alpha}\theta + a\right]\cos\theta \tag{10}$$

When $$\frac{dx}{dy} = 0$$

the slope of the curve ACDE is infinite and the curve is vertical, or parallel to the Y axis. Thus:

$$\frac{dx}{dy} = \frac{\frac{dx}{d\theta}}{\frac{dy}{d\theta}} \text{ when } \frac{dx}{dy} = 0 \quad \frac{dx}{d\theta} = 0$$

Therefore, from equation (9) the curve is vertical when $$\frac{\left(\frac{h}{\sin\alpha} - a\right)}{\alpha}\cos\theta - \left[\frac{\left(\frac{h}{\sin\alpha} - a\right)}{\alpha}\theta + a\right]\sin\theta = 0 \tag{11}$$

The width of the curve ACDE may be given by the x coordinate from the parametric equation (7) at angle θ. Therefore the desired minimum lift of the spreader relative to the central axis 170 can be substituted for x, giving:

$$\left[\frac{\left(\frac{h}{\sin\alpha} - a\right)}{\alpha} \cdot \theta + a\right]\cos\theta = \text{minimum lift from axis 170} \tag{12}$$

Equations 11 and 12 thus form a system of non linear simultaneous equations with 2 variables (θ and a). The value of h may be chosen to correspond to the desired maximum lift of the spreader 100 from the central axis 170. A desired width of the flat surfaces corresponding to maximum lift (e.g., surfaces 120, 122) may also be chosen. The angle α corresponds to the angle from the central axis to an edge of the flat surface of maximum lift as may be seen in FIG. 4. Thus values for h, α, and minimum lift are known constants. Therefore equations 11 and 12 can be solved by numerical means for θ and a. Equations (11) and (12) may be solved numerically by the fixed point iteration method or the Newton-Raphson method, for example. The cam curve ACDE may then be plotted using either the polar form (equation (6)) or the parametric form (equations (7) and (8)).

Once the curve ACDE has been plotted along with the other components of the graph of FIG. 4, the area bounded by BCDFG may be used as a cross sectional pattern which defines a single quadrant of the distal end 105 of the spreader 100. To create a full cross section of the distal end 105, the area BCDFG may be reflected about the Y axis and the resulting graph reflected about the X axis. The resulting cross section may appear similar to FIG. 3 but with all dimensions known. Using the full cross section as a pattern, the distal end 105 of the spreader 100 may be constructed according to known techniques and materials. In one embodiment, the resulting spreader will result in a maximum force or lift when rotated approximately 60 degrees from the position of minimum lift.

Figure 5:
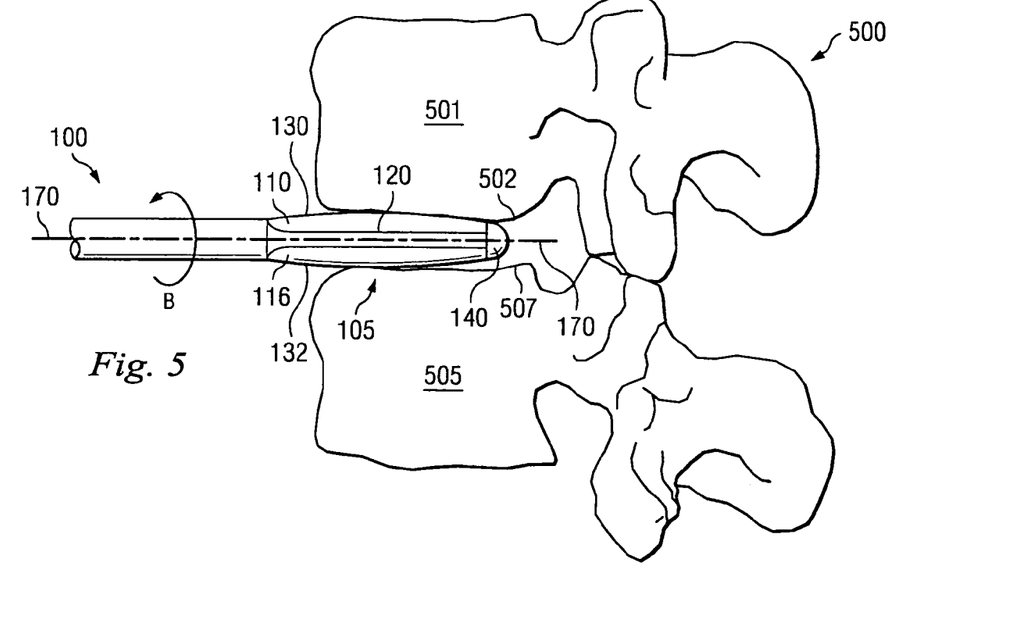
FIG. 5 is a diagram of a constant lift cam spreader between two adjacent vertebrae in a minimum lift position.

FIG. 5 is a diagram of a constant lift cam spreader 100 in a minimum lift position between two adjacent vertebrae 501, 505. FIG. 5 provides an example of one environment 500 in which one embodiment of the constant lift cam spreader 100 may operate. The surgical site 500 may be cleaned and an incision made that allows the spreader 100 access to the vertebrae 501, 505. In a fusion or disc replacement procedure, the disc (not shown) interposing the vertebrae 501, 505 may be perforated or removed to allow insertion of the spreader 100. As previously described, the spreader 100 may also be driven directly into tissue such as the spinal disc such that the initial perforation is made by the sharpened tip 140.

The distal end 105 of the spreader 100 may be inserted between the vertebra 501, 505 in a position of minimum lift. Thus minimum lift surfaces 130, 132 may be in substantially solid contact with the endcaps 502, 507 of vertebrae 501, 505, respectively. To effect distracting, or spreading, of the vertebrae 501, 505, the spreader 100 may be rotated about the central axis 170. The spreader 100 may be designed such that rotation in either direction results in the same distraction. Here the spreader is rotated counter clockwise in the direction of arrow B.

Figure 6:
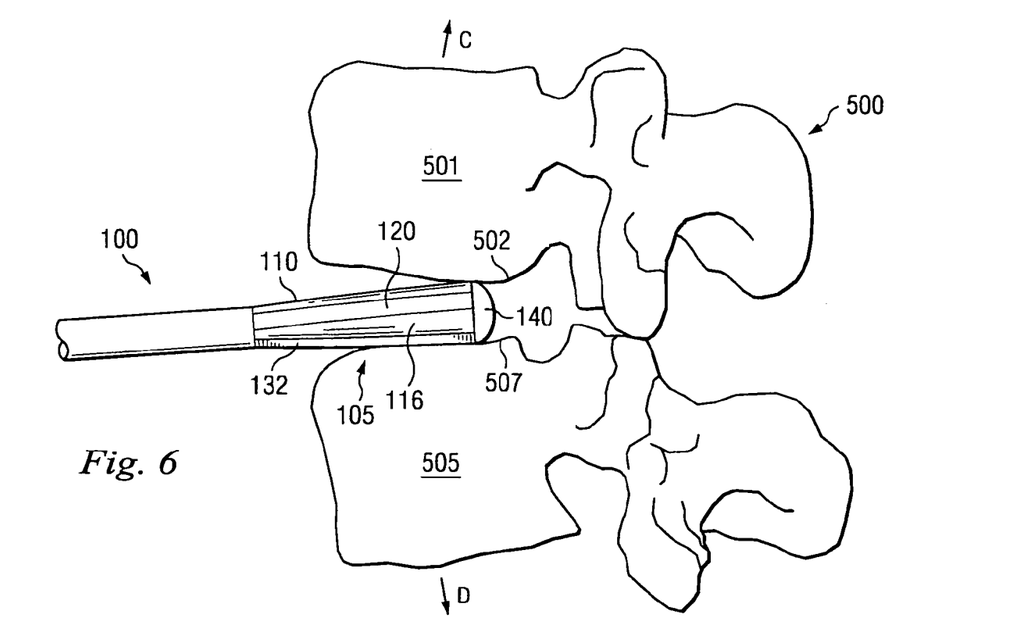
FIG. 6 is a diagram of a constant lift cam spreader between two adjacent vertebrae in a partially lifted position.

FIG. 6 is a diagram of a constant lift cam spreader 100 between two adjacent vertebrae 501, 505 in a partially lifted position. As the spreader 100 is rotated about axis 170 in the direction of arrow B, the minimum lift surfaces 130, 132 are replaced as the primary contact surface to the endcaps 502, 507 by cam lobes 110, 114, respectively. Thus the distance between the vertebrae 501, 505 begins to increase as a result of the increasing lift provided by the spreader 100. Here, the vertebrae 501, 505 may displace from one another in the general direction of arrows C and D, respectively. The displacement of the vertebrae may be more easily controlled and stress to the end plates 502, 507 minimized due to the constant rate of incremental lift relative to the amount of rotation of the tool 100.

If so desired, the spreader 100 may provide increasing lift or displacement commensurate with the degree of rotation about the axis 170 until the endcaps contact 502, 507 come into contact with maximum lift surfaces 120, 122, respectively. When the desired amount of lift has been achieved, the remaining steps of the surgical procedure may be carried out. For example, a spacer device, such as is described in U.S. Pat. Ser. No. 10/404,262, the disclosure of which is hereby incorporated by reference, can be inserted into the distracted disc space. The spreader 100 may also be rotated in an opposite direction (e.g., clockwise) to provide a proportionate decrease in lift relative to the amount of opposite rotation. The spreader 100 may be rotated completely back to the minimum lift position in preparation for retraction from between the vertebrae 501, 505.

The foregoing has outlined features of several embodiments according to aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A cam spreader comprising:
   an elongated portion comprising a handle and a longitudinal axis extending along its length;
   a cam portion extending from the elongated portion, the cam portion comprising:
      a substantially flat first lateral surface and an opposing substantially flat second lateral surface, the lateral surfaces extending substantially parallel to one another and separated by a first width, the lateral surfaces configured to engage a pair of adjacent vertebrae in a first position providing a first amount of lift to the vertebrae;
      a substantially flat upper surface and an opposing substantially flat lower surface, the upper and lower surfaces extending substantially parallel to one another and substantially perpendicular to the lateral surfaces, the upper and lower surfaces separated by a first height defining a second amount of lift, the first height being greater than the first width, the upper and lower surfaces configured to engage the pair of adjacent vertebrae in a second position providing a second amount of lift greater than the first amount lift;
      a first arcuate surface extending between the upper surface and the first lateral surface;
      a second arcuate surface extending between the first lateral surface and the lower surface;
      a third arcuate surface extending between the lower surface and the second lateral surface; and
      a fourth arcuate surface extending between the second lateral surface and the upper surface;
   wherein the first arcuate surface and the second arcuate surface are not defined by a single continuous arc and wherein the third arcuate surface and the fourth arcuate surface are not defined by a single continuous arc;
   wherein the first, second, third, and fourth arcuate surfaces are configured such that as the cam portion is rotated about the longitudinal axis between the first position and the second position the increase in lift between the first amount of lift and the second amount of lift is directly proportional to the degree of rotation.

2. The spreader of claim 1, wherein the elongated portion and the cam portion are monolithic.

3. The spreader of claim 1, wherein the first and second arcuate surfaces are substantially symmetrical to each other about a first reflection plane, the longitudinal axis extending within the first reflection plane and the first reflection plane being substantially perpendicular to the lateral surfaces.

4. The spreader of claim 3, wherein the third and fourth arcuate surfaces are substantially symmetrical to each other about the first reflection plane.

5. The spreader of claim 4, wherein the third and fourth arcuate surfaces are substantially symmetrical to the first and second arcuate surfaces about a second reflection plane, the second reflection plane being substantially perpendicular to the upper and lower surfaces and the first reflection plane.

6. The spreader of claim 1,
   wherein an origin is located at the intersection of the longitudinal axis, a second axis, and a third axis, the second axis being perpendicular to the longitudinal axis and the lateral surfaces, the second axis extending equidistant from the upper and lower surfaces and passing through a midpoint of each of the lateral surfaces, the third axis being perpendicular to the longitudinal axis and the upper and lower surfaces, the third axis passing extending equidistant from the lateral surfaces and passing through a midpoint of each of the upper and lower surfaces;

wherein a cross-sectional profile of the first arcuate surface, as viewed in a cross-sectional plane defined by the second and third axes, is defined by a portion of a plot of a curve given by the mathematical equation, $$l = \frac{\left(\frac{h}{\sin\alpha} - a\right)}{\alpha} \theta + a,$$

where l is the distance from the first arcuate surface to the origin in the cross-sectional plane, θ is an independent variable representing the angle relative to the second axis of a line extending from the origin to the first arcuate surface, h is half of the first height, α is the angle relative to the second axis of a line extending from the origin to an intersection of the upper surface and the first arcuate surface, and a is a variable representing the distance from the origin to an intersection of the plot of the curve and the second axis.

7. The spreader of claim 6, wherein the value of the parameter a is selected from the group of solutions to the simultaneous equations:

$$\frac{\left(\frac{h}{\sin\alpha} - a\right)}{\alpha} \cos\theta - \left[\frac{\left(\frac{h}{\sin\alpha} - a\right)}{\alpha} \theta + a\right] \sin\theta = 0, \text{ and}$$

$$\left[\frac{\left(\frac{h}{\sin\alpha} - a\right)}{\alpha} \cdot \theta + a\right] \cos\theta = w,$$

for θ=[0,π/2], where w is half of the first width.

8. A distractor for distracting a pair of adjacent vertebrae, the distractor comprising:

an elongated body having a proximal portion, a distal portion, and a longitudinal axis extending therebetween;

a handle extending from the proximal portion of the elongated body; and a cam portion extending from the distal portion of the elongated body, the cam portion comprising:

a substantially flat first surface;

a substantially flat second surface extending substantially parallel to the first surface and spaced from the first surface by a first distance, the first distance corresponding to a first distraction height;

a substantially flat third surface extending substantially perpendicular to the first surface;

a substantially flat fourth surface extending substantially parallel to the third surface and spaced from the third surface by a second distance, the second distance corresponding to a second distraction height, the second distraction height being greater than the first distraction height;

a first curved surface extending between the first surface and the third surface;

a second curved surface extending between the third surface and the second surface;

a third curved surface extending between the second surface and the fourth surface; and a fourth curved surface extending between the fourth surface and the first surface;

wherein the first curved surface and the second curved surface are not defined by a single continuous arc;

wherein the cam portion is rotatable between a first position where the first and second surfaces interface with the adjacent vertebrae and distract the adjacent vertebrae by the first distraction height and a second position where the third and fourth surfaces interface with the adjacent vertebrae and distract the adjacent vertebrae by the second distraction height;

wherein at least two of the first, second, third, and fourth curved surfaces interface with the adjacent vertebrae as the cam portion is rotated between the first and second positions, and wherein the at least two curved surfaces that interface with the adjacent vertebrae are configured such that a distraction height of the cam portion is changed in direct proportion to the degree of rotation between the first distraction height and the second distraction height.

9. The distractor of claim 8, wherein each of the first, second, third, and fourth curved surfaces are configured such that the distraction height of the cam portion is changed in direct proportion to the degree of rotation.

10. The distractor of claim 8, wherein the elongated body and the cam portion are monolithic.

11. The distractor of claim 8, wherein the cam portion is removably attached to the elongated body.

12. The distractor of claim 8, wherein the substantially flat first and second surfaces are equidistant from the longitudinal axis.

13. The distractor of claim 12, wherein the substantially flat third and fourth surfaces are equidistant from the longitudinal axis.

14. The distractor of claim 8, wherein the third curved surface and the fourth curved surface are not defined by a single continuous arc.

15. A method of designing a cross-sectional profile for a distractor and manufacturing a distractor having a first pair of substantially flat surfaces for maintaining a first distraction height and a second pair of substantially flat surfaces for maintaining a second distraction height, the method comprising:

selecting a first displacement height;

selecting a second displacement height greater than the first displacement height;

selecting a maximum length for at least one of the second pair of substantially flat surfaces;

plotting a cross-sectional rendering of the first and second pairs of substantially flat surfaces on a two dimensional graph with x and y axes based on the selected first and second displacement heights and the selected maximum length;

plotting a portion of a curve defined by the equation:

$$l = \frac{\left(\frac{h}{\sin\alpha} - a\right)}{\alpha} \theta + a$$

to connect at least one of the plotted first pair of surfaces to at least one of the plotted second pair of surfaces, where l is the distance from the curve to an intersection of the x and y axes, θ is an independent variable representing an angle relative to the x-axis of a line extending from the intersection of the x and y axes to the curve, a is a selected variable parameter, h is half of the second displacement height, and α is an angle relative to the x-axis of a line extending from the intersection of the x and y axes to an end of at least one of the plotted second pair of surfaces;

plotting reflections of the plotted portion of the curve about the x and y axes to define a bounded area between the first and second pairs of surfaces, the plotted portion of the curve, and the plotted reflections, the bounded area defining the cross-sectional profile of the distractor; and forming a distractor having the cross-sectional profile defined by the bounded area.

16. The method of claim 15, wherein the value of the parameter a is selected from the group of solutions obtained by solving the simultaneous equations:

$$\frac{\left(\frac{h}{\sin\alpha} - a\right)}{\alpha} \cos\theta - \left[\frac{\left(\frac{h}{\sin\alpha} - a\right)}{\alpha} \theta + a\right] \sin\theta = 0, \text{ and}$$

$$\left[\frac{\left(\frac{h}{\sin\alpha} - a\right)}{\alpha} \cdot \theta + a\right] \cos\theta = w,$$

for θ=[0,π/2], where w is half of the first displacement height.

* * * * *